United States Patent [19]
Margolin

[11] Patent Number: 5,518,729
[45] Date of Patent: May 21, 1996

[54] COMPOSITIONS AND METHODS FOR REPARATION AND PREVENTION OF FIBROTIC LESIONS

[76] Inventor: Solomon B. Margolin, 6723 Desco Dr., Dallas, Tex. 75225

[21] Appl. No.: 243,058

[22] Filed: May 16, 1994

Related U.S. Application Data

[63] Continuation-in-part of Ser. No. 59,214, May 7, 1993, abandoned, and Ser. No. 947,995, Sep. 21, 1992, Pat. No. 5,310,562, and a continuation of Ser. No. 64,831, May 19, 1994, abandoned, said Ser. No. 947,995, is a continuation of Ser. No. 737,914, Jul. 26, 1991, abandoned, which is a continuation-in-part of Ser. No. 440,978, Nov. 22, 1989, abandoned.

[51] Int. Cl.$^6$ .............................. A61K 9/02; A61K 9/14; A61K 9/20; A61K 9/48

[52] U.S. Cl. .................. 424/423; 424/427; 424/434; 424/436; 424/451; 424/464; 424/489; 514/824; 514/838; 514/851; 514/866; 514/913

[58] Field of Search .................... 424/464, 451, 424/489, 423, 427, 436, 435

[56] References Cited

U.S. PATENT DOCUMENTS 3,974,281  8/1976  Gadekar .................... 424/263

Primary Examiner—Thurman K. Page
Assistant Examiner—James M. Spear
Attorney, Agent, or Firm—John H. Crozier

[57] ABSTRACT

In a preferred embodiment, drugs having pharmacological properties which are useful in the medicinal therapy of fibrotic disease for the reparation and prevention of fibrotic lesional tissues, such drugs including as the active ingredient one or more N-substituted 2-(1H) pyridone(s). The composition of this invention is novel as an anti-fibrotic drug, namely, as an agent for treating fibrosis. Any existing compounds have not been shown to be effective for the reparation and prevention of fibrotic lesions.

12 Claims, 1 Drawing Sheet

\# COMPOSITIONS AND METHODS FOR REPARATION AND PREVENTION OF FIBROTIC LESIONS

CROSS-REFERENCE TO RELATED APPLICATION

This is a continuation-in-part of application Ser. No. 08/059,214 filed on May 7, 1993, now abandoned. This application is also a continuation of application Ser. No. 08/064,831, filed on May 19, 1994, now abandoned. The present application is a continuation-in-part of U.S. application Ser. No. 07/947,995, filed Sep. 21, 1992, now U.S. Pat. No. 5,310,562, issued May 10, 1994, which is a continuation of U.S. application Ser. No. 07/737,914, filed Jul. 26, 1991, abandoned, which is a continuation-in-part of U.S. application Ser. No. 07/440,978, filed Nov. 22, 1989, now abandoned.

BACKGROUND OF THE INVENTION

1. Field of the Invention

The present invention relates to medical compositions and methods for the reparation of fibrotic lesional tissues and the prevention of fibrotic lesions, which compositions comprise one or more N-substituted 2(1-H) pyridones and/or one or more N-substituted 3(1H) pyridones as active anti-fibrotic ingredient(s).

2. Background Art

Herein, the term "anti-fibro", "anti-fibrotic" or "anti-fibrosis" refers to the reparations and/or prevention of pathological polymerization of collagen in lung fibrosis, arteriosclerosis, prostatic hypertrophy, keloid, myocarditis, collagen disease, scar, wrinkle, etc., and reparation as well normalization of the existing pathological fibrotic tissues.

Methods of preparation of some N-substituted 2(1-H) pyridones useful in the present invention are described in U.S. Pat. No. 3,839,346, issued Oct. 1, 1974, to Gadekar, and titled N-SUBSTITUTED PYRIDONE AND GENERAL METHOD FOR PREPARING PYRIDONES, the disclosure of which is incorporated by reference hereinto. That patent also describes use of those compounds in analgesic, anti-inflammatory, and anti-pyretic treatments. U.S. Pat. Nos. 3,974,281, issued Aug. 10, 1976; 4,042,699, issued Aug. 16, 1977; and 4,052,509, issued Oct. 4, 1977, all to Gadekar, describe further use of one of these compounds, 5-methyl-1-phenyl-2(1H) pyridone ("pirfenidone"), in lowering serum uric acid and glucose levels, treating upper respiratory inflammatory conditions, and treating inflammatory skin conditions, in humans and other mammals.

The use of pirfenidone in the reparation and prevention of fibrotic lesions is described in the above-referenced copending U.S. application Ser. No. 07/947,995, filed Sep. 21, 1992, U.S. Pat. No. 5,310,562 the disclosure of which is incorporated by reference hereinto.

It has been discovered by the present inventor that other N-substituted 2(1-H) pyridone compounds and/or N-substituted 3-( 1H) pyridone(s) also have anti-fibrotic activity. Heretofore, before the discoveries of the inventions disclosed herein and in the above copending application, no effective pharmacological agent or composition has been available for the prevention or removal of pathologic fibrotic lesions of the lungs, prostate glands, musculoskeletal diseases, myocardial degeneration, myocardial infarction, arteriosclerosis, and other lesional fibroses.

For example, powerful anti-inflammatory glucocorticoids (hormones relating to carbohydrate metabolism) such as hydrocortisone or prednisolone administered in very large doses have repeatedly been shown to be ineffective against fibrotic disease. These glucocorticoids do not arrest or remove such life-threatening fibrotic lesions. The glucocorticoids may be effective, however, as anti-inflammatory agents under such condition that they may temporarily ameliorate the secondary acute inflammation flare-ups which intermittently occur in tissues or organs damaged by fibrotic disease. Indeed, excessive and prolonged administration of glucocorticoids in pulmonary fibrotic disease may cause destruction of tissues, due to fibrosis or an exacerbation and acceleration of the fibrotic destruction.

Antopol (1950) was the first of many investigators who found that the anti-inflammatory glucocorticoids readily enhance fibrotic degeneration of lung tissues. Similarly, the non-steroidal anti-inflammatory agents such as aspirin, salicylates, phenylbutazone, indomethacin, various phenylacetic acid derivatives, and the like have also failed to arrest formation of, or cause repair of progressive, chronic fibrotic damage to lung tissues, prostatic tissues, musculoskeletal tissues, etc.

Accordingly, it is a principal object of the present invention to provide compositions for the reparation and prevention of fibrotic lesional tissue.

It is an additional object of the invention to provide such compositions that comprise one or more N-substituted 2-(1H) pyridone(s) and/or N-substituted 3-(1H) pyridone(s) as active anti-fibrotic ingredient(s).

Other objects of the present invention, as well as particular features and advantages thereof, will be elucidated in, or be apparent from, the following description.

SUMMARY OF THE INVENTION

The present invention overcomes the limitations of the prior art by providing, in a preferred embodiment, drugs having pharmacological properties which are useful in the medicinal therapy of fibrotic disease for the reparation and prevention of fibrotic lesional tissues, such drugs including as the active ingredient one or more N-substituted 2-(1H) pyridone(s) and/or N-substituted 3-(1H) pyridone(s). The compositions of this invention are novel as an anti-fibrotic drug, namely, as an agent for treating and preventing fibrosis. Any existing compounds have not been shown to be effective for the reparation and prevention of fibrotic lesions. The active ingredient exerts an anti-fibrotic activity quite dissimilar to and independent of fibrinolytic activity.

DETAILED DESCRIPTION OF THE PREFERRED EMBODIMENTS

Figure 1:
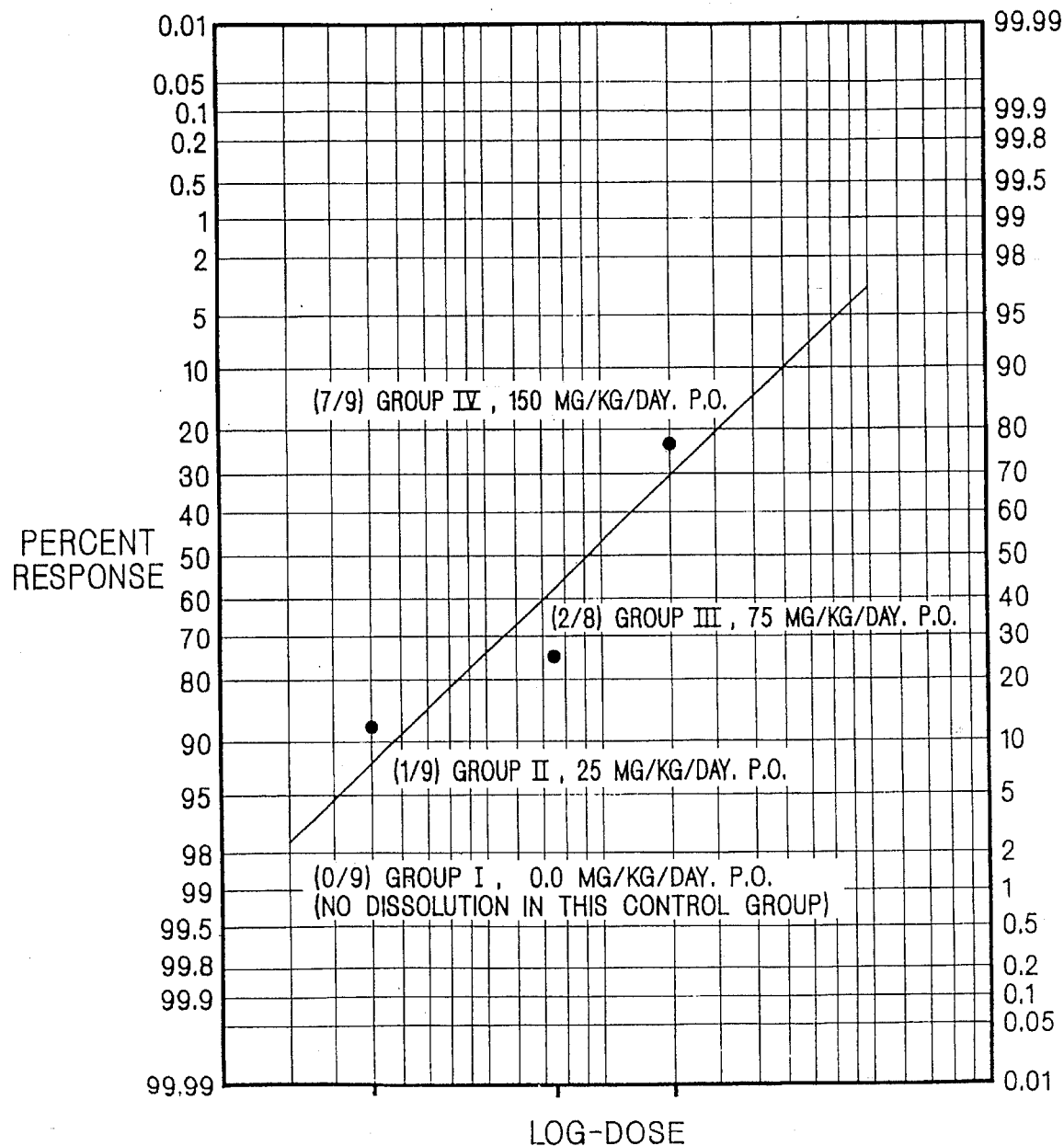
FIG. 1 is a graph showing the anti-fibrotic activity in relation to the dosage of anti-fibrotic active agent administered.

The "anti-fibrotic" activity described herein differs from "fibrinolytic" or "anti-fibrin" activity. The "fibrinolytic" or "anti-fibrin" activity refers to the biological ability of a pharmaceutical substance to (1) prevent fibrin formation (prevent formation of a blood clot) or (2) lyse or dissolve a previously formed blood clot.

The "anti-fibrotic" activity discovered by the present inventor and as used herein refers to the ability of an active substance to (1) prevent an excessive pathologic accumulation of collagenous scar or connective tissue in various body structures and organs (usually triggered by some injury, allergy, infection, or by some inherited genetic aberration), or (2) cause the non-surgical removal or biological dissolution of an existing excessive and pathologic accumulation of fibrotic collagenous tissue (for example, as in the dissolution of life-threatening fibrotic lesions of the lung found in patients with asbestosis).

A. CONNECTIVE TISSUE PROTEINS OF MAMMALS

Three major classifications of connective tissue proteins are recognized with the largest portions consisting of collagen types (70 to 80%) and elastin types (15 to 20%). A miscellaneous group constitutes the third and smallest class.

The general biochemical characteristics of the collagen types which constitute the principal protein (1) in normal white connective tissue and (2) in scar or fibrotic tissue, are summarized in Table 1, as contrasted with elastin types. For example, collagen is sparingly soluble in water, but readily converted to water soluble gelatin upon boiling in an acid or alkali. In contrast, the highly water soluble elastin does not convert to gelatin upon boiling in an acid or alkali.

The elastin constitutes the principal protein of yellow connective tissue found in elastic structures such as the walls of larger blood vessels and walls of lung alveoli.

Investigations on the molecular biochemical level of tissues have demonstrated a very slow turnover rate for metabolic processes involving fibrotic lung collagen. In fact, the metabolic rate is measured in years. By contrast, the metabolic rates of the other connective tissue collagens including elastin and the like are measured and expressed in hours and days (White, Handler, and Smith, 1973, page 983).

B. INTERSTITIAL PROLIFERATION (HYPERPLASIA) OF FIBROBLAST-TYPE CELLS IN LUNGS AND OTHER ORGAN TISSUES

The synthesis of various collagens found in scar or fibrotic structures takes place in fibroblast cells which then extrude the collagen into the surrounding matrix. During this wound repair process, there are (1) a rapid proliferation and increase in the number of fibroblasts at the site, and (2) a sharp rise in the rate of the synthesis and extrusion of collagen. If these two phenomena are not prevented, the pathologic and progressive accumulation of collagen would cause polymerization and fibrotic disease (for example, impairment of respiratory function, impaired circulatory function via fibrotic changes in arterial walls, fibrotic degeneration of renal and liver function, degenerative musculoskeletal function, fibrotic degeneration of cardiac muscle or skeletal muscle, fibrotic degenerative changes in neuronal tissues in the central nervous system as well as the peripheral nervous system, etc.). [S. L. Robbins, R. S. Cotrans, V. Kumar, "Pathologic Basis of Disease", 6th edition, pages 40–84, Saunders, Philadelphia, Pa. (Pub.)].

With pulmonary interstitial fibrotic hyperplasia, small and firm nodules are palpable throughout the lung tissue, and upon gross examination are recognized from their opaque, airless structure to be foci of abnormal accumulations of fibrotic connective tissue. Such foci vary in size and color according to their age. Their aggressive and continued enlargement and coalescence ultimately leads to collagenous solidification of large segments of the lungs.

These enlarging foci also impinge upon the lung capillaries thereby to reduce pulmonary blood flow, and at the same time, impede lymphatic drainage from the lungs. As a consequence, exudate accumulates within the alveoli, and secondary thickening of the alveolar wall ensues. These interacting processes sharply reduce the efficiency of the gaseous exchange in the lung alveoli, which is a primary function of the normal lung.

In addition, these pulmonary fibrotic alternations and accumulations raise the pulmonary blood vessel resistance and lead to cor pulmonale (sharply elevated pulmonary blood pressure). Prolonged elevated pulmonary blood pressure almost invariably leads to congestive heart failure in addition to the cyanosis caused by inadequate pulmonary exchange of oxygen and carbon dioxide. The prognosis is poor and the incidence of severe morbidity and deaths is high.

Furthermore, the fibrosis of the lung impairs the physiological and biochemical functions of the lung that are independent of the pulmonary gas exchange (oxygen and carbon dioxide) role of the lungs cited above. These Include:

(1) filtration, degradation, and removal of the following substances:

(a) aged leucocytes from the blood, and (b) particulate matter (for example, tissue cell debris, blood cell aggregates, inert foreign matter, small thrombi); and (2) synthesis of adequate supplies of heparin.

Heparin is a useful substance that normally prevents the formation of life-threatening blood clots in the major blood vessels (for example, cerebral and coronary blood vessels).

C. DIFFERENTIATION BETWEEN ANTI-FIBROTIC ACTIVITY AND ANTI-INFLAMMATORY ACTIVITY

Pharmacological anti-fibrotic activity as exemplified by the arrest and removal of lung scarring (interstitial hyperplasia and fibrotic foci), or pathologic fibrotic lesions in other organs and tissues described herein, is clearly distinct from and independent of any pharmacological anti-inflammatory activity.

The debilitating pathologic degeneration of organs and tissues affected by fibrotic disease continues for extended periods of time, measured in months or years, beyond the short-term (hours and days) of exacerbating inflammatory flare-ups (classical clinical and histophathological signs of edema, local heat, and leucocytic infiltration have disappeared).

The compositions of this invention are effective for treatment of disease caused by the pathologic and excessive fibrotic accumulations such as pulmonary fibrosis, benign prostate hypertrophy, coronary infarcts, cerebral infarcts, myocardiac fibrosis, musculoskeletal fibrosis, post-surgical adhesions, liver cirrhosis, real fibrotic disease, fibrotic vascular disease (atherosclerosis, varix, or varicose veins), scleroderma, Alzheimer's disease, diabetic retinopathy, glaucoma, etc. The pulmonary fibrosis may have been chemically induced, for example, by the anti-cancer drugs bleomycin or cyclophosphamide or by the weed killer paraquat. The compositions of this invention not only arrest the formation of new fibrotic tissue but causes removal of previously formed fibrotic collagen-containing tissue. These pharmacological properties were heretofore unknown.

The present invention arrests formation of or causes removal of a pathogenic accumulation of water-insoluble collagenous connective tissue (for example, excessive scar or lesional fibrotic tissue, etc.). By medicinally removing such pathologic collagenous tissue in fibrotic lungs, the invention eliminates or prevents:

(1) the mechanical compression or occlusion (stenosis) of blood vessels (for example, pulmonary arteries, veins, and capillaries), pulmonary bronchioles, and alveoli;

(2) the inhibition of the primary respiratory function of the alveoli of the lungs, namely, the exchange of oxygen and carbon dioxide gases; and (3) the increased pulmonary blood vessel resistance (cor pulmonale) which readily causes fatal congestive heart failure because of the excessive workload on cardiac muscle that is engendered by the cor pulmonale.

D. TREATMENT WITH PIRFENIDONE

As is described in the above-referenced U.S. application Ser. No. 07/947,995, U.S. Pat. No. 5,310,562 the dramatic and novel pulmonary anti-fibrotic activity of pirfenidone has been observed and demonstrated in laboratory animal experiments (rats, hamsters, dogs) and in humans. The anti-fibrotic activity in cardiac infarctions, benign prostatic hypertrophy, and post-operative adhesions has been observed in humans. The renal anti-fibrotic activity has been demonstrated in hamsters. In every instance, the anti-fibrotic activity was clearly distinct from any anti-inflammatory properties.

The acute toxicity of the ingredient in the medical composition of the present invention which exerts the anti-fibrotic activity is as shown in the table below:

| | ACUTE TOXICITY (LD: mg/kg) | | | |
|---|---|---|---|---|
| | Route for Administration | | | |
| Animal | p.o. (number) | i.v. (number) | i.p. (number) | 10% Ointment p.o. (number) |
| Mouse: | 997.7(40) | 285 ± 5(50) | 600 ± 43(60) | 11,500 ± 1,100(43) |
| Rat; | | | | |
| Male: | 1,295(25) | | 430 ± 29(42) | 12,500(10) |
| Female: | 2,300(30) | | | |
| Guinea Pig: | 810 ± 25(30) | | 460 ± 28(25) | |
| Rabbit: | | 280 ± 32(12) | | |
| Cat: | 500(17) | 40(4) | | |
| Dog: | 300(11) | 200(6) | | |
| Monkey: | | 100(3) | | |

The anti-fibrotic activity measured against pulmonary fibrosis was found to be quite dissimilar to and independent of anti-flammatory activity when these activities were assayed in rats and hamsters. Experiments in dog and human clinical trials affirm these findings. Pirfenidone has been extensively studied for oral anti-fibrotic activity in laboratory animals and in humans. The anti-fibrotic effect in pulmonary fibrosis was demonstrated upon oral administration:

(1) in diets or by gavage to rat or hamsters,
(2) oral capsules in dogs, and
(3) oral administration to humans.

EXAMPLE 1

The results of a histopathological examination of the lungs of rats for fibrosis (interstitial hyperplasia) after receiving 300 mg/kg body weight of pirfenidone in the diet for three months are summarized in Table 2. The individual microscopic readings of the lung are also shown in Table 2, where a score schedule of 0, 1, 2, and 3 reflects the degree of fibrosis.

The data in Table 2 reveal a statistically significant reduction in the amount of fibrosis in rats receiving pirfenidone as compared to placebo control rats (Group 1). The mean score for the controls (Group 1) was 1.63±0.23, and for Group IV (pirfenidone, 300 mg/kg body weight daily was 0.95±0.23.

Student's T value was 2.43, with P less than 0.02 (highly significant statistically).

In male and female Beagle dogs, the anti-fibrotic activity was found to be a direct function of the dosage of pirfenidone administered, a classical pharmacological dose-response (Table 3, FIG. 1). Lung tissues examined microscopically, and scored on a schedule of 0, 1, 2, and 3 for fibrosis resulted in clear demonstration of statistically significant reduction in pulmonary fibrosis in dogs given the drug as compared to control animals.

The mean score for Group I (Control) was 2.11±0.31, and for Group IV, which received pirfenidone, 150 mg/kg per day orally in capsules, was 0.22±0.19.

In hamsters, pulmonary fibrosis induced with crysotile asbestos was removed following oral pirfenidone (Table 4).

This anti-fibrotic activity was not simply a a palliative (relieving) effect.

The asbestos-induced fibrosis did not recur after the pirfenidone had been discontinued for two months.

In mice, pulmonary fibrosis induced with cyclophosphamide was removed following oral administration of pirfenidone and an immunosuppresant drug in humans and is know to produce pulmonary fibrosis in patients as a side effect.

A similar experience has been observed in trials on human patients with pulmonary fibrosis caused by asbestos.

For the first time ever, pirfenidone makes possible a pulmonary resolution process whereby a life-threatening solidified fibrotic lung disease can be restored to a relatively normal tissue where the alveoli are no longer collapsed or occluded. That is, the microscopic examination reveals that the tissues are regenerated and become normal, spongy lungs.

The novel role of pirfenidone in the therapeutic repair of fibrotic lung tissue featuring removal of fibrotic lesions, and concomitant regeneration of normal lung tissue has been observed in experimental asbestosis by histopathological examination of lung tissue specimens under the light microscope, and electron microscopy (Table 4).

Very little, if any, fibrotic alterations are seen after treatment with adequate doses of pirfenidone.

A further novel discovery was the demonstration under the electron microscope that the lung cell-imbedded asbestos fibers which had initiated and maintained the extensive fibrotic lesions also had been removed. This was subsequently confirmed by ashing of lung specimens in a laboratory oven, and then determining the asbestos content.

The discovery of this additional novel "clearing" property of pirfenidone for the first time affords a therapeutic pharmacological remedy for chronic respiratory disease caused by the inhalation and accumulation in the lungs of harmful foreign matter from polluted air, asbestos, industrial dust (grain, lime, fertilizers, cotton fibers, glass fibers, plastics, coal, etc.), resulting in asbestosis, silicosis, and/or black lung of miners, for example.

TABLE 1

CONTRAST BETWEEN PROPERTIES OF COLLAGEN AND ELASTIN

| Property | Collagen | Elastin |
|---|---|---|
| 1. Water soluble | − | + |
| 2. Converts to gelatin on boiling | + | − |
| 3. Primarily in white connective tissue | + | − |
| 4. Primarily in yellow connective tissue | − | + |
| 5. Primarily associated with highly elastic structure (e.g., blood vessels) | − | + |
| 6. Primarily in organ structural tissue; fibrotic or scar tissue (e.g., lung fibrosis, etc.) | + | − |
| 7. Metabolic turnover rate | low | high |

TABLE 2

| | | Lung Connective Tissue Score | | | |
|---|---|---|---|---|---|
| Animal Number | Sex | 0 | 1 | 2 | 3 |
| GROUP I (CONTROL) | | | | | |
| 104 | F | | | | X |
| 8 | M | | | X | |
| 72 | F | X | | | |
| 74 | F | | | | X |
| 75 | F | | X | | |
| 80 | F | | | | X |
| 81 | F | | | | X |
| 82 | F | | X | | |
| 88 | F | | | X | |
| 94 | F | | X | | |
| 1 | M | | X | | |
| 19 | M | | X | | |
| 26 | M | | | X | |
| 36 | M | | X | | |
| 43 | M | | | | X |
| 45 | M | X | | | |
| 52 | M | | X | | |
| 53 | M | | | | X |
| 55 | M | | | X | |
| Total: | | 2 | 8 | 4 | 5 |
| Mean: 1.63 | | | | | |
| S.E. 0.23 | | | | | |
| GROUP IV: PIRFENIDONE 300 mg/kg (p.o.) | | | | | |
| 95 | F | | | X | |
| 86 | F | | | | X |
| 93 | F | | X | | |
| 97 | F | X | | | |
| 98 | F | | X | | |
| 99 | F | | X | | |
| 119 | F | | X | | |
| 122 | F | | X | | |
| 123 | F | X | | | |
| 135 | F | X | | | |
| 5 | M | | X | | |
| 11 | M | | X | | |
| 16 | M | | X | | |
| 29 | M | X | | | |
| 31 | M | X | | | |
| 32 | M | | X | | |
| 34 | M | | | X | |
| 35 | M | | | X | |
| 40 | M | | | X | |
| Total: | | 5 | 11 | 2 | 1 |
| Mean: 0.95 | | | | | |
| S.E.: 0.18 | | | | | |
| t: 2.43 | | | | | |
| P: <0.02 | | | | | |

TABLE 3

EFFECT OF ORAL PIRFENIDONE UPON PULMONARY INTERSTITIAL HYPERPLASIA (FIBROSIS) IN DOGS

| Group | Number of Dogs | Hyperplasia Scores* | | | | Average Scores | Incidence of Normal Lung |
|---|---|---|---|---|---|---|---|
| | | 0 | 1 | 2 | 3 | | |
| I. Control (0.0%) | 9 | 0 | 3 | 2 | 4 | 2.11 ± 10.31 | 0/9 |
| II. Pirfenidone (16.7%) 25 mg/kg/day | 6 | 1 | 1 | 4 | 0 | 1.50 ± 0.34 | 1/6 |
| III. Pirfenidone (25.0%) 75 mg/kg/day | 8 | 2 | 2 | 3 | 1 | 1.38 ± 0.38 | 2/8 |
| IV. Pirfenidone 150 mg/kg/day | 9 | 7 | 2 | 0 | 0 | 0.22 ± 0.15** | 7/9 |

*Degree of Hyperplasia (fibrosis)
0 = normal tissue
1 = minimal
2 = moderate
3 = severe
**Highly Statistically Significant (P < 0.001)

TABLE 4

EFFECT OF ORAL PIRFENIDONE UPON ASBESTOS-INDUCED PULMONARY INTERSTITIAL FIBROSIS IN HAMSTERS

| Group | Animal Number | Lung Density | Pulmonary Fibrosis Score | |
|---|---|---|---|---|
| | | | Light Microscope | Electron Microscope |
| I. Control No Asbestos (−); No Pirfenidone | 1 | 0.95 | 0 | 0 |
| | 2 | 0.90 | 1 | 0 |
| | 3 | 1.05 | 1 | 1 |
| | 4 | 1.10 | 0 | 0 |
| Average | | 1.00 ± 0.05 | 0.50 ± 0.25 | 0.25 ± 0.25 |
| II. Asbestos (+); No Pirfenidone (−) | 5 | 2.70 | 3 | 3 |
| | 6 | 1.90 | 2 | 3 |
| | 7 | 2.53 | 3 | 2 |
| | 9 | 2.98 | 3 | 3 |
| Average | | 2.53 ± 0.23 | 2.75 ± 0.25 | 2.75 ± 0.25 |
| III. Asbestos (+)*; Plus Pirfenidone (+) | 10 | 0.98 | 0 | 0 |
| | 12 | 1.04 | 2 | 1 |
| | 13 | 1.26 | 1 | 0 |
| | 14 | 1.41 | 1 | 0 |
| Average | | 1.17 ± 0.10 | 1.00 ± 0.41 | 0.25 ± 0.25 |

TABLE 4-continued

EFFECT OF ORAL PIRFENIDONE UPON ASBESTOS-INDUCED PULMONARY INTERSTITIAL FIBROSIS IN HAMSTERS

| Group | Animal Number | Lung Density | Pulmonary Fibrosis Score Light Microscope | Pulmonary Fibrosis Score Electron Microscope |
|---|---|---|---|---|
| Student's "T" Values: | | | | |
| Group II vs. Group III: | | 5.9** | 3.7** | 7.1** |
| Group II vs. Group I: | | 6.5** | 5.9** | 7.1** |

Degree of Fibrosis:
0 = normal tissue
1 = minimal
2 = moderate
3 = severe
*Asbestos by inhalation for 5 days; Pirfenidone, 500 mg/kg/day, orally in the diet for two months, beginning two months after the five-day exposure to asbestos dust.
**Highly Statistically Significant (P < 0.001).

TABLE 5

EFFECT OF ORAL PIRFENIDONE UPON CYCLO-PHOSPHAMIDE-INDUCED INTERSTITIAL FIBROSIS IN MICE

| No. Mice | Lung Dry Wt. Mg. | Lung OH-Proline MicGm/Lung | Lung OH-Proline MicGm/Mg | Lung FIBROSIS Scores## (N/N) |
|---|---|---|---|---|
| GROUP I-A (cyclophosphamide only, 200 mg/kg, i.p.) | | | | |
| 10 | 50.0 ± 1.3 | 313 ± 10 | 6.01 ± .24 | 4.43 ± 43 (0/5) |
| GROUP I-B (cyclophosphamide only, 200 mg/kg, i.p.) | | | | |
| 8 | 46.8 ± 2.3 | 406 ± 21 | 8.85 ± 0.58 | 3.90 ± 0.23(0/5) |
| COMBINED GROUPS I-A AND I-B (cyclophosphamide only, 200 mg/kg, i.p.) | | | | |
| 18 | 48.9 ± 1.3 | 360 ± 18 | 7.50 ± 0.44 | 4.34 ± 0.26(0/10) |
| GROUP II (cyclophosphamide, 200 mg/kg, i.p., plus pirfenidone, 500 mg/kg/day, p.o.) | | | | |
| 10 | 52.4 ± 0.9 | 284 ± 13** | 5.46 ± 0.31** | 2.99 ± 0.75(3/5)* |
| GROUP III (saline control; no cyclophosphamide; no pirfenidone) | | | | |
| 6 | 45.3 ± 1.2 | 317 ± 20 | 7.00 ± 0.42 | 0.26 ± 0.15(5/5)# |
| GROUP IV (pirfenidone, 500 mg/kg/day, p.o.; saline; no cyclophosphamide) | | | | |
| 6 | 39.0 ± 2.8** | 288 ± 9** | 7.60 ± 0.60 | 0.68 ± 0.35**(5/5)# |

**Differs significantly (P < 0.01) frm Combined Groups I-A and I-B (Student T test for differences between means).
Differs significantly (P < 0.05) from Combined Groups I-A and I-B (Chi-square two-fold contingency table; incidence of scores 3.0 or less).
Scoring (0 through 6) of lung interstitial hyperplasia and fibrotic nodule formation based on technique recommended by the Pneumoconiosis Committee of the College of American Pathologists, and the National Institute for Occupational Safety and Health (Ref: Arch. Path. Lab. Med., vol. 106,1982).

Clinical human open trials have been undertaken as follows:

1. Pulmonary fibrosis diagnosed as caused by asbestos was treated with pirfenidone and closely and objectively followed in two subjects. Clinical impressions were dramatic and highly favorable.

2. Pulmonary fibrosis diagnosed as idiopathic in nature was treated with pirfenidone and closely and objectively followed in one subject for over two years. Clinical impressions were highly favorable.

3. Benign prostate hypertrophy in three elderly subjects (66–100 years) was treated with pirfenidone with very good to excellent clinical results. Two subjects suffered from frequency, severe nocturia, incontinence, constant urgency, and in the third these symptoms were less severe. Clinically, all had enlarged prostates that explained the symptoms. The results were dramatic in the eldest subject within two weeks of therapy. Nocturia of 6–7 trips (every 60–90 minutes) per night was reduced to 1 or 2 nightly (4–5 hours apart). In the other two patients, nocturia 3–4 times (every 2–3 hours) was reduced to once nightly 4–5 hours after retiring. In all cases digital examination of the prostate revealed a detectable reduction in the size of the prostate in 3–4 weeks.

4. Fibrosis of the ventricular myocardium, an outcome of repeated coronary infarcts was treated with pirfenidone in one subject (diagnosed as terminal), with objective evidence of the reduction of the fibrosis (electrocardiogram maps and nuclear resonance determinations). The subject lived for an additional three years, despite the fact that the administration of the drug was terminated after 18 months, due to a limited supply.

5. Inhibition of excessive scar formation by direct application of pirfenidone ointment to skin lesions in 10 cases. Mild to moderate skin laceration or lesions failed to generate skin scars, or caused only minimal scarring when pirfenidone ointment was directly applied to the lesion.

Examples of medical preparations include: (1) capsules, (2) tablets, (3) powders, (4) granules, (5) syrups, (6) injection (intravenous, intramuscular, or drip administration), (7)

cream, (8) ointment, (9) inhalation, (10) eye drop, (11) suppositories, (12) pills, etc.

The above preparations are available. Among them, capsules, injections, cream, and ointments are preferred preparations.

TEST EXAMPLE 1

In one capsule, 800 mg, 1200 mg, or 1600 mg of pirfenidone is contained.

TEST EXAMPLE 2

Hydrophilic ointment containing 5 to 10% pirfenidone.

The average oral dosage for anti-fibrotic activity in humans is 3600 milligrams per day, with a range of from about 2400 milligrams to about 4800 milligrams per day. Administration may be in divided dosage—for example, 1200 milligrams three times per day.

E. COMPOSITIONS AND DOSAGES FOR THE PRESENT INVENTION

The above-referenced U.S. Pat. No. 3,839,346 describes methods of preparation of some N-substituted 2-(1H)-pyridones useful in the present invention. Those pyridones are:
5-Methyl-1-(3-nitrophenyl-2)-(1H) pyridone
5-Methyl-1-(4'-methoxyphenyl)-2-(1H) pyridone
5-Methyl-1-p-tolyl-2-(1H) pyridone
5-Methyl-1-(3'-trifluoromethylphenyl)-2-(1H)-pyridone
1-(4'Chlorophenyl)-5-Methyl-2)-(1H) pyridone
5-Methyl-1-(2'-naphthyl)-2-(1H) pyridone
5-Methyl-1-(1'naphthyl)-2-(1H) pyridone
3-Methyl-1-phenyl-2-(1H) pyridone
6-Methyl-1-phenyl-2-(1H) pyridone
3,6-Dimethyl-1-phenyl-2-(1H) pyridone
5-Methyl-1-(2'-Thienyl)-2-(1H) pyridone
1-(2'-Furyl)-5-Methyl-2-(1H) pyridone
5-Methyl-1-(5'-quinolyl)-2-(1H) pyridone
5-Methyl-1-(4'-pyridyl)-2-(1H) pyridone
5-Methyl-1-(3'-pyridyl)-2-(1H) pyridone
5-Methyl-1-(2'-pyridyl)-2-(1H) pyridone
5-Methyl-1-(2'-quinolyl)-2-(1H) pyridone
5-Methyl-1-(4'-quinolyl)-2-(1H ) pyridone
5-Methyl-1-(2'-thiazolyl)-2-(1H) pyridone
1-(2'-Imidazolyl)-5-Methyl-2-(1H) pyridone
5-Ethyl-1-phenyl-2-(1H) pyridone
1-Phenyl-2-(1H) pyridone
1-(4'-Nitrophenyl)-2-(1H) pyridone
1,3-Diphenyl-2-(1H) pyridone
1-Phenyl-3-(4'-chlorophenyl)-2-(1H) pyridone
1,3-Diphenyl-5-methyl-2-(1H) pyridone
3-(4'-Chlorophenyl)-5-Methyl-1-phenyl-2-(1H) pyridone
5-Methyl-3-phenyl-1-(2'-thienyl)-2-(1H) pyridone Additionally, the following N-substituted 3-(1H) pyridones, useful in the present invention, can be prepared using methods similar to those set forth in the above-referenced U.S. Pat. No. 3,839,346:
5-Methyl-1-phenyl-3-(1H) pyridone
5-Methyl-1-(4'-methoxyphenyl)-3-(1H) pyridone
5-Methyl-1-p-tolyl-3-(1H) pyridone
1-(4'-Chlorophenyl)-5-methyl-3-(1H) pyridone
5-Methyl-1-(2'-naphthyl)-3-(1H) pyridone
4-Methyl-1-phenyl-3-(1H) pyridone
6-Methyl-1-phenyl-3-(1H) pyridone
5-Methyl-1(2'-Thienyl)-3-(1H) pyridone
1-(2'-Furyl)-5-methyl-3-(1H) pyridone
5-Methyl-1-(5'-quinolyl)-3-(1H) pyridone
5-Methyl-1-(3'-pyridyl)-3-(1H) pyridone
5-Methyl-1-(2'-pyridyl)-3-(1H) pyridone
5-Methyl-1-(2'-quinolyl)-3-(1H) pyridone
5-Ethyl-1-phenyl-3-(1H) pyridone
1-Phenyl-3-(1H) pyridone Effective dosages and rates of application of the compositions of the present invention have been found to be effective, or can be expected to be effective, in a range of from about one-quarter to about twice the dosages given above for pirfenidone.

The compositions of the present invention may be administered in forms consisting of capsules, tablets, powders, granules, syrups, injectable fluids, pills, creams, ointments, inhalable fluids, eye drops, and suppositories.

While the invention has been described in detail and with reference to specific embodiments thereof, such have been provided for purposes of illustrating the invention and are not intended as limitations thereon. It will thus be apparent to one skilled in the art that various changes and modifications can be made therein without departing from the spirit and the scope of the present invention.

I claim:

1. A method for the reparation of, and prophylaxis against, fibrotic lesional tissue in a mammal, comprising administering internally to said mammal a pharmaceutical composition having one or more compounds selected from the group consisting of N-substituted 2-(1H) pyridones and N-substituted 3-(1H) pyridones as active anti-fibrotic ingredient(s), said composition being administered to said mammal at a rate of from about 5 mg per kilogram of body weight per day to about 300 mg per kilogram of body weight per day, said group excluding 5-methyl-1-phenyl-2-(1H) pyridone, but including, exclusively, 5-Methyl-1-(3-nitrophenyl- 2)-(1H) pyridone, 5-Methyl-1-(4'-methoxyphenyl)-2-(1H) pyridone, 5-Methyl-1-p-tolyl-2-(1H) pyridone, 5-Methyl- 1-(3'-trifluoromethylphenyl)-2-(1H)-pyridone, 1-( 4'Chlorophenyl)-5-Methyl-2)-(1H) pyridone, 5-Methyl-1-(2'-naphthyl)- 2-(1H) pyridone, 5-Methyl-1-(1'naphthyl)-2-(1H) pyridone, 3-Methyl-1-phenyl-2-(1H) pyridone, 6-Methyl-1-phenyl- 2-(1H) pyridone, 3,6-Dimethyl-1-phenyl-2-(1H) pyridone, 5-Methyl-1-(2'-Thienyl)-2-(1H) pyridone, 1-(2'-Furyl)- 5-Methyl-2-(1H) pyridone, 5-Methyl-1-(5'-quinolyl)-2-( 1H) pyridone, 5-Methyl-1-(4'-pyridyl)-2-(1H) pyridone, 5-Methyl- 1-(3'-pyridyl)-2-(1H) pyridone, 5-Methyl-1-(2'-pyridyl)- 2-(1H) pyridone, 5-Methyl-1-(2'-quinolyl)-2-(1H) pyridone, 5-Methyl-1-(4'-quinolyl)-2-(1H) pyridone, 5-Methyl- 1-(2'-thiazolyl)-2-(1H) pyridone, 1-(2'-Imidazolyl)-5-Methyl- 2-(1H) pyridone, 5-Ethyl-1-phenyl-2-(1H) pyridone, 1-Phenyl- 2-(1H) pyridone, 1-(4'-Nitrophenyl)-2-(1H) pyridone, 1,3-Diphenyl- 2-(1H) pyridone, 1-Phenyl-3-(4'-chlorophenyl)-2-( 1H) pyridone, 1,3-Diphenyl-5-methyl-2-(1H) pyridone, 3-(4'-Chlorophenyl)- 5-Methyl-1-phenyl-2-(1H) pyridone, 5-Methyl-3-phenyl- 1-(2'-thienyl)-2-(1H) pyridone, 5-Methyl-1-phenyl-3-( 1H) pyridone, 5-Methyl-1-(4'-methoxyphenyl)-3-(1H) pyridone, 5-Methyl-1-p-tolyl-3-(1H) pyridone, 1-(4'-Chlorophenyl)- 5-methyl-3-(1H) pyridone, 5-Methyl-1-(2'-naphthyl)- 3-(1H) pyridone, 4-Methyl-1-phenyl-3-(1H) pyridone, 6-Methyl-1-phenyl-3-(1H) pyridone, 5-Methyl-1(2'-Thienyl)- 3-(1H) pyridone, 1-(2'-Furyl)-5-methyl-3-(1H) pyridone, 5-Methyl-1-(5'-quinolyl)-3-(1H) pyridone, 5-Methyl-1-(3'-pyridyl)-3-(1H) pyridone, 5-Methyl-1-(2'-pyridyl)-3-( 1H) pyridone, 5-Methyl-1-(2'-quinolyl)-3-(1H) pyridone, 5-Ethyl- 1-phenyl-3-(1H) pyridone, and 1-Phenyl-3-(1H) pyridone.

2. A method, as defined in claim 1, further comprising administering said pyridone(s) in an amount of from about 25 mg to about 9600 mg per day.

3. A method, as defined in claim 1, further comprising administering said pyridone(s) in an amount of from about 75 mg to about 9600 mg per day.

4. A method, as defined in claim 1, further comprising administering said pyridone(s) in an amount of from about 25 mg to about 3200 mg contained in a capsule.

5. A method, as defined in claim 1, wherein said fibrotic lesional tissue is associated with a condition in the group consisting of pulmonary fibrosis, benign prostate hypertrophy, coronary infarcts, cerebral infarcts, myocardiac fibrosis, musculoskeletal fibrosis, post-surgical adhesions, liver cirrhosis, renal fibrotic disease, fibrotic vascular disease, scleroderma, Alzheimer's disease, diabetic retinopathy, and skin lesions.

6. A method, as defined in claim 1, wherein said pharmaceutical composition is administered by means selected from the group consisting of capsules, tablets, powders, granules, syrups, injectable fluids, creams, ointments, inhalable fluids, eye drops, suppositories, and pills.

7. A method, as defined in claim 1, wherein said mammal is a human.

8. A method for the reparation of, and prophylaxis against, fibrotic lesional tissue in a mammal, comprising administering topically to said mammal a pharmaceutical composition containing one or more compounds selected from the group consisting of N-substituted 2-(1H) pyridones and N-substituted 3-(1H) pyridones as active anti-fibrotic ingredient(s) in an amount of from about 1% to about 20%, said group excluding 5-methyl-1-phenyl-2-(1H) pyridone, but including, exclusively, 5-Methyl-1-(3-nitrophenyl-2)-(1H) pyridone, 5-Methyl-1-(4'-methoxyphenyl)-2-(1H) pyridone, 5-Methyl- 1-p-tolyl-2-(1H) pyridone, 5-Methyl-1-(3'-trifluoromethylphenyl)- 2-(1H)-pyridone, 1-(4'Chlorophenyl)-5-Methyl- 2)-(1H) pyridone, 5-Methyl-1-(2'-naphthyl)-2-(1H) pyridone, 5-Methyl-1-(1'naphthyl)-2-(1H) pyridone, 3-Methyl- 1-phenyl-2-(1H) pyridone, 6-Methyl-1-phenyl-2-(1H) pyridone, 3,6-Dimethyl-1-phenyl-2-(1H) pyridone, 5-Methyl-1-(2'-Thienyl)- 2-(1H) pyridone, 1-(2'-Furyl)-5-Methyl-2-(1H) pyridone, 5-Methyl-1-(5'-quinolyl)-2-(1H) pyridone, 5-Methyl-1-(4'-pyridyl)-2-(1H) pyridone, 5-Methyl-1-(3'-pyridyl)-2-( 1H) pyridone, 5-Methyl-1-(2'-pyridyl)-2-(1H) pyridone, 5-Methyl- 1-(2'-quinolyl)-2-(1H) pyridone, 5-Methyl-1-(4'-quinolyl)- 2-(1H) pyridone, 5-Methyl-1-(2'-thiazolyl)-2-(1H) pyridone, 1-(2'-Imidazolyl)-5-Methyl-2-(1H) pyridone, 5-Ethyl- 1-phenyl-2-(1H) pyridone, 1-Phenyl-2-(1H) pyridone, 1-( 4'-Nitrophenyl)-2-(1H) pyridone, 1,3-Diphenyl-2-(1H) pyridone, 1-Phenyl-3-(4'-chlorophenyl)-2-(1H) pyridone, 1,3-Diphenyl- 5-methyl-2-(1H) pyridone, 3-(4'-Chlorophenyl)-5-Methyl- 1-phenyl-2-(1H) pyridone, 5-Methyl-3-phenyl-1-(2'-thienyl)- 2-(1H) pyridone, 5-Methyl-1-phenyl-3-(1H) pyridone, 5-Methyl-1-(4'-methoxyphenyl)-3-(1H) pyridone, 5-Methyl-1-p-tolyl-3-(1H) pyridone, 1-(4'-Chlorophenyl)-5-methyl-3-(1H) pyridone, 5-Methyl-1-(2'-naphthyl)-3-(1H) pyridone, 4-Methyl- 1-phenyl-3-(1H) pyridone, 6-Methyl-1-phenyl-3-(1H) pyridone, 5-Methyl-1(2'-Thienyl)-3-(1H) pyridone, 1-(2'-Furyl)-5-methyl- 3-(1H) pyridone, 5-Methyl-1-(5'-quinolyl)-3-(1H) pyridone, 5-Methyl-1-(3'-pyridyl)-3-(1H) pyridone, 5-Methyl- 1-(2'-pyridyl)-3-(1H) pyridone, 5-Methyl-1-(2'-quinolyl)-3-( 1H) pyridone, 5-Ethyl-1-phenyl-3-(1H) pyridone, and 1-Phenyl- 3-(1H) pyridone.

9. A method, as defined in claim 8, wherein said fibrotic lesional tissue is associated with a condition in the group consisting of musculoskeletal fibrosis, post-surgical adhesions, scleroderma, glaucoma, and skin lesions.

10. A method, as defined in claim 8, wherein said pharmaceutical composition is administered by means selected from the group consisting of creams, ointments, hydrophillic ointments, inhalable fluids, eye drops, and suppositories.

11. A method, as defined in claim 1, wherein the compound selected is 5-ethyl-1-phenyl-2-(1H) pyridone.

12. A method, as defined in claim 8, wherein the compound selected is 5-ethyl-1-phenyl-2-(1H) pyridone.

* * * * *

UNITED STATES PATENT AND TRADEMARK OFFICE
CERTIFICATE OF CORRECTION

PATENT NO. : 5,518,729
DATED : May 21, 1996
INVENTOR(S) : Solomon B. Margolin

It is certified that error appears in the above-indentified patent and that said Letters Patent is hereby corrected as shown below:

In the Abstract at line 5, following "pyridone(s)", is inserted:

---and/or N-substituted 3-(1H) pyridone(s)---.

Signed and Sealed this

Tenth Day of September, 1996

*Attest:*

BRUCE LEHMAN

*Attesting Officer*  *Commissioner of Patents and Trademarks*